(12) United States Patent
Hahn et al.

(10) Patent No.: US 7,407,743 B2
(45) Date of Patent: Aug. 5, 2008

(54) KIT AND METHOD OF SCREENING WILSON'S DISEASE

(75) Inventors: Si Houn Hahn, Rochester, MN (US); Young-Ju Jang, Gyeonggi-do (KR); Soo-Young Lee, Gyeonggi-do (KR); Ha-Cheol Shin, Gyeonggi-do (KR); Sun-Young Park, Gyeonggi-do (KR); Eun-Sun Yu, Gyeonggi-do (KR); Hee-Sung Han, Seoul (KR)

(73) Assignee: Zenovac, Inc (KR), Seocho-Gu (KR)

( * ) Notice: Subject to any disclaimer, the term of this patent is extended or adjusted under 35 U.S.C. 154(b) by 226 days.

(21) Appl. No.: 10/934,693

(22) Filed: Sep. 7, 2004

(65) Prior Publication Data

US 2005/0042693 A1  Feb. 24, 2005

Related U.S. Application Data

(63) Continuation-in-part of application No. 09/965,126, filed on Sep. 26, 2001, now Pat. No. 6,806,044.

(30) Foreign Application Priority Data

Mar. 31, 2001  (KR) .................... 10-2001-0017100

(51) Int. Cl.
*G01N 33/48* (2006.01)
*G01N 33/53* (2006.01)
*G01N 33/537* (2006.01)
*G01N 33/543* (2006.01)
*C12Q 1/00* (2006.01)
*C12Q 1/26* (2006.01)
*C12Q 1/28* (2006.01)

(52) U.S. Cl. .............. 435/4; 435/7.1; 435/7.2; 435/7.92; 435/70.21; 435/25; 435/28; 435/338; 435/975

(58) Field of Classification Search ................. 435/25, 435/28, 4, 975, 7.1
See application file for complete search history.

(56) References Cited

U.S. PATENT DOCUMENTS 5,491,066 A * 2/1996 Hiyamuta et al. ........... 435/7.4
6,806,044 B2 * 10/2004 Hahn et al. ..................... 435/4

OTHER PUBLICATIONS

Ohura T, Abukawa D, Shiraishi H, Yamaguchi A, Arashima S, Hiyamuta S, Tada K, Linuma K, Pilot study of screening for Wilson disease using dried blood spots obtained from children seen at outpatient clinics, J. Inher. Met. Dis., 1999, 22: 74-80.*

(Continued)

*Primary Examiner*—Anish Gupta
*Assistant Examiner*—Julie Ha
(74) *Attorney, Agent, or Firm*—Sughrue Mion, PLLC

(57) ABSTRACT

The present invention relates to a method for measuring a ceruloplasmin concentration, and more particularly, to a method for measuring a ceruloplasmin in a blood spot based on a standard concentration curve obtained through an enzyme-linked immunosorbent assay (ELISA) or a dissociation-enhanced time-resolved fluoroimmunoassay using a ceruloplasmin-specific polyclonal antibody or a ceruloplasmin-specific monoclonal antibody.

3 Claims, 3 Drawing Sheets

OTHER PUBLICATIONS

Hiyamuta S and Ito K, Monoclonal Antibody Against the Active Site of Caeruloplasmin and the ELISA System Detecting Active Caeruloplasmin, Hybridoma, 1994, 13(2): 139-141.*

Hahn S, Lee SY, Jang YJ, Kim SN, Shin HC, Park SY, Kang JH and You ES, Development of a Screening Kit for Early Diagnosis and Prevention of Wilson's Disease, Journal of Korean Pediatrics Association, 2001, 44(12):1374-1380.*

Si Houn Hahn et al., "Pilot study of mass screening for Wilson's disease in Korea", *Molecular Genetics and Metabolism*, vol. 76, 2002, pp. 133-136.

* cited by examiner

Lane S, standard; lane 1, CP only (10 ug);
Lane 2, MoAb 2-1.1; Lane 3, MoAb 1-2.1;
Lane 4, CP + MoAb 2-1.1;
Lane 5, CP + MoAb 1-2.1

KIT AND METHOD OF SCREENING WILSON'S DISEASE

CROSS-REFERENCE TO RELATED APPLICATIONS

This application is a continuation-in-part of a application entitled "Method of measuring ceruloplasmin concentration in a blood spot, kit and method of diagnosing Wilson's disease," U.S. application Ser. No. 09/965,126, filed on Sep. 26, 2001 now U.S. Pat. No. 6,806,044, of which the entire disclosure is hereby incorporated by reference.

BACKGROUND OF THE INVENTION

1. Field of the Invention

The present invention relates to a method for measuring ceruloplasmin concentration. More specifically, the present invention relates to a method for measuring ceruloplasmin concentration on a blood spot using a standard curve of concentration obtained through an enzyme-linked immunosorbent assay (ELISA) or a dissociation-enhanced time-resolved fluoroimmunoassay using a specific polyclonal antibody or a monoclonal antibody of the ceruloplasmin.

The method for measuring ceruloplasmin concentration on a blood spot is very useful for screening of Wilson's disease in population.

2. Description of the Related Art

In 1912, Samuel Alexander Kinnier Wilson first described the detailed clinical and pathologic findings of 4 patients, all of whom, he believed, had the same disease as progressive lenticular degeneration in association with hepatic cirrhosis. One in 25,000 to 30,000 people is suffering from an autosomal recessive disease, one of common genetic diseases with a carrier rate of 1/90. Wilson's disease is a copper metabolism defect, that is, copper is not easily excreted through a biliary tract nor is incorporated into ceruloplasmin. Therefore, copper is accumulated in the liver, brain, cornea, red blood cell and kidney, causing hepatic dysfunction including hepatitis, liver cirrhosis, neurologic disturbance like dysarthria, dystonia, tremors, and hemolytic anemia, or renal tubular dysfunction, etc.

Unfortunately, most patients with Wilson's disease are diagnosed after liver cirrhosis or neurologic damage already developed. Although liver transplantation is available, many of them suffer to die or live with severe neurologic sequelae. However, if the diagnosis is made at an early stage of clinical course, they can have a normal life back by starting an early treatment with an orally applied chelating agent, e.g., D-penicillamine or trienthylene tetramine, without developing any further complications. Therefore, early diagnosis and treatment is very important to Wilson's disease.

One of the most valuable indexes to diagnose Wilson's disease is level of ceruloplasmin in blood. Ceruloplasmin has a molecular weight of 132,000 and 6–7 atoms of copper per molecule. Normally, ceruloplasmin is a plasma protein and contains 95% of the total circulating copper in a body. It also performs various functions, for example, carrying copper to internal tissues, promoting aromatic amine oxidase activation and antioxidation, eliminating free radicals and hydrogen peroxide ($H_2O_2$), and controlling inflammatory reaction. In general, a normal person has 20–50 mg/dl of ceruloplasmin in the serum, but Wilson's disease patients have reduced level of ceruloplasmin. Normally, ceruloplasmin has an oxidase activity and exists as a copper-containing form ("holoceruloplasmin"). Also, normal persons excrete copper efficiently and have little apoceruloplasmin without the oxidase activity inside of the body. In contrast, Wilson's disease patients, in spite of having the equal amount of apoceruloplasmin to that of the normal persons, have little holoceruloplasmin (2.7±2.0 mg/dl) due to failure of copper incorporation into apoceruloplasmin.

Therefore, it is very important to quantify the ceruloplasmin (holoceruloplasmin) in blood, to diagnose Wilson's disease. However, in case of neonates, the screening test is ineffective to trace any sign of the disease since they normally have a low ceruloplasmin concentration. Generally, the best time to start the screening test would be several months after birth, when the ceruloplasmin concentration reaches adult level.

The conventional method for measuring ceruloplasmin in the related art includes a method for measuring holoceruloplasmin through measurement of oxidase activity of ceruloplasmin, a radial immunodiffusion assay, or an immunoturbidimetric assay.

These methods require a large amount of blood to conduct the assays, and the sera in the blood need to be separated from the whole blood by centrifugation. Even after the sera are obtained, samples need to be frozen before carrying or storing to prevent the degradation of proteins in the sera. Therefore, the methods in the related art are not the best way to perform the mass screening test in that they require extra work for collecting, carrying and storing the specimen. Since the number of the specimen obtained at once is limited, a nationwide screening test requiring a large number of the specimen could not be carried out with the conventional methods.

SUMMARY OF THE INVENTION

It is, therefore, an object of the present invention to provide a method for measuring ceruloplasmin concentration in a blood spot using a standard curve obtained by either an enzyme-linked immunosorbent assay (ELISA) or a dissociation-enhanced time-resolved fluoroimmunoassay employing a specific polyclonal antibody and a monoclonal antibody of ceruloplasmin.

An another object of the present invention is to provide a method for making an early diagnosis of Wilson's disease through a quantitative analysis of ceruloplasmin in blood spot based on a sandwich ELISA method using two antibodies, for example, two monoclonal antibodies, one monoclonal antibody and one polyclonal antibody or two polyclonal antibodies. One of two antibodies recognizes an epitope that plays an important role for the oxidase activity of ceruloplasmin and the other recognizes other epitope in the same ceruloplasmin molecule.

It is still another object of the present invention to provide a method for manufacturing a ceruloplasmin-specific polyclonal antibody using a serum produced from a rabbit immunized with a purified human ceruloplasmin containing holoceruloplasmin.

It is still another object of the present invention to provide a method for manufacturing a ceruloplasmin-specific monoclonal antibody using a hybridoma cell line obtained through fusion of mouse spleen cells with myeloma cells, selection and cultivation of fused spleen cells to produce an monoclonal antibody, and the spleen cells were obtained from an immunized mouse with the purified ceruloplasmin containing the holoceruloplasmin.

It is still another object of the present invention to provide a method for obtaining an absorbance standard curve according to a sandwich method of an enzyme-linked immunosorbent assay by applying a ceruloplasmin-specific polyclonal antibody and a ceruloplasmin-specific monoclonal antibody conjugated with horseradish peroxidase, respectively to a standard blood spot and a control reference blood spot manufactured.

It is still another object of the present invention to provide a method for obtaining a fluorescence standard curve according to a sandwich method of a dissociation-enhanced time-resolved fluoroimmunoassay by applying a ceruloplasmin-specific polyclonal antibody and a ceruloplasmin-specific monoclonal antibody conjugated with europium, respectively to a standard blood spot and a control reference blood spot manufactured.

It is still another object of the present invention to provide a diagnostic reagent for Wilson's disease and a screening kit of the same in order to measure the holoceruloplasmin concentration in a blood spot using a standard concentration curve obtained through an enzyme-linked immunosorbent assay or a dissociation-enhanced time-resolved fluoroimmunoassay employing a holoceruloplasmin-specific polyclonal antibody and a holoceruloplasmin-specific monoclonal antibody, a manufacturing method of a standard blood spot and a control reference blood spot.

It is still another object of the present invention to provide a new method of a quantitative analysis of copper-containing holoceruloplasmin based on an enzyme-linked immunosorbent assay or a dissociation-enhanced time-resolved fluoroimmunoassay on a blood spot obtained from young infants or children that is collected using a blood filter paper.

The present invention further provides a hybridoma which produces a monoclonal antibody which does not neutralize oxidase activity of holoceruloplasmin.

These and other aspects will become evident by reference to the description of the invention.

BRIEF DESCRIPTION OF DRAWINGS

In FIG. 5, the terms "CP," "MoAB 2-1.1," and "MoAB 1-2.1" indicate "ceruloplasmin," "monoclonal antibody 2-1.1," and "monoclonal antibody 1-2.1," respectively.

DETAILED DESCRIPTION OF THE INVENTION

Figure 1:
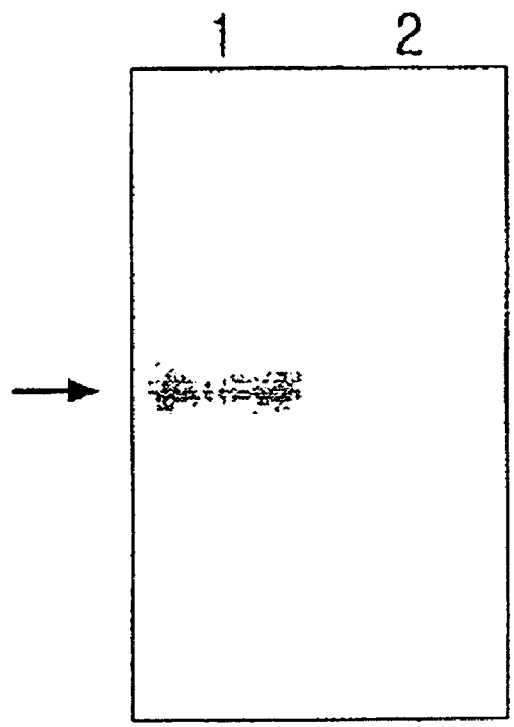
FIG. 1 shows that a purified ceruloplasmin oxidizes p-phenylenediamine to form a purple band (lane 1), while a ceruloplasmin mixed with a ceruloplasmin-specific antibody loses its oxidase activity and does not form a band (lane 2).

The present invention allows an early detection of Wilson's disease through a quantitative analysis of holoceruloplasmin extracted from a blood spot by using an immunoassay method such as the enzyme-linked immunosorbent assay or dissociation enhanced time-resolved fluoroimmunoassay. In one preferred embodiment, the present invention employs a blood spot that is easy to collect, carry and store in order to be able to measure a large number of specimens at once. As the method of the present invention detects and quantifies holoceruloplasmin with high sensitivity and accuracy, the detection can be performed by using a small amount of blood sample, preferably, a blood spot on a filter paper of 1.5 mm punch.

The detection or quantification of the holoceruloplasmin in a sample can be carried out by an immunoassay utilizing the binding reaction between an antibody and holoceruloplasmin. Various immunoassays are well-known in the art and any of them can be employed. Examples of the immunoassays include sandwich method employing the monoclonal antibody and another monoclonal antibody as primary and secondary antibodies, respectively, sandwich methods employing the monoclonal antibody and a polyclonal antibody as primary and secondary antibodies, sandwich methods employing the polyclonal antibody and a polyclonal antibody as primary and secondary antibodies, staining methods employing gold colloid, agglutination method, latex method and chemical luminescence. Among these, especially preferred is sandwich enzyme-linked immunosorbent assay (ELISA) or dissociation-enhanced time-resolved fluoroimmunoassay (DELFIA). The ELISA and DELFIA are well-known to one of ordinary skill in the art.

In these methods, a primary antibody is immobilized on, for example, the bottom of each well of microtiter plate and then a sample containing a target protein is reacted with the immobilized primary antibody. After washing, a secondary antibody conjugated with either horse radish peroxidase or europium is reacted with the antigen which was captured by primary antibody. After washing, the amount of antigen is quantified using standard curve. As the primary antibody, a polyclonal or monoclonal antibody which does not neutralize the oxidase activity of ceruloplasmin may be employed. As the secondary antibody, a monoclonal or polyclonal antibody, which does not neutralize the oxidase activity of ceruloplasmin but recognizes a different epitope from the primary antibody, may be used.

In one preferred embodiment, the monoclonal antibodies, which do not neutralize oxidase activity of ceruloplasmin and recognizes a different epitope, may be the monoclonal antibody 2-1.1 or 1-2.1.

The quantification of the secondary antibody may be carried out by measuring the label (e.g., enzyme or lanthanide) on the secondary antibody. Horseradish peroxidase and europium may be preferably employed as an enzyme and lanthanide, respectively.

According to the present invention, the inventors developed a method for measuring holoceruloplasmin concentration in a blood spot using enzyme-linked immunosorbent assay of the present invention, the method comprising the steps of:

manufacturing a ceruloplasmin-specific polyclonal antibody;

manufacturing a ceruloplasmin-specific monoclonal antibody;

conjugating horseradish peroxidase to the ceruloplasmin-specific polyclonal antibody and the ceruloplasmin-specific monoclonal antibody;

manufacturing a standard blood spot and a control reference blood spot by adding a purified ceruloplasmin solution containing holoceruloplasmin to a ceruloplasmin-free blood to a predetermined concentration;

obtaining an absorbance standard concentration curve based on the standard blood spot and the control reference blood spot using the ceruloplasmin-specific polyclonal antibody and the ceruloplasmin-specific monoclonal antibody; and measuring holoceruloplasmin concentration in a blood spot of a patient according to a standard concentration curve through an enzyme-linked immunosorbent assay.

In addition, the present invention provides a method for measuring holoceruloplasmin concentration in a blood spot according to the dissociation-enhanced time-resolved fluoroimmunoassay of the present invention, the method comprising the steps of:

manufacturing a ceruloplasmin-specific polyclonal antibody;

manufacturing a ceruloplasmin-specific monoclonal antibody;

conjugating europium ($Eu^{3+}$) to the ceruloplasmin-specific polyclonal antibody and the ceruloplasmin-specific monoclonal antibody;

manufacturing a standard blood spot and a control reference blood spot by adding a purified ceruloplasmin solution containing holoceruloplasmin to a ceruloplasmin-free blood to a predetermined concentration;

obtaining a fluorescence standard concentration curve based on the standard blood spot and the control reference blood spot using the ceruloplasmin-specific polyclonal antibody and the ceruloplasmin-specific monoclonal antibody; and measuring holoceruloplasmin concentration in a blood spot from a patient according to the fluorescence standard concentration curve through a dissociation-enhanced time-resolved fluoroimmunoassay.

The ceruloplasmin-specific polyclonal antibody acts as an antigen and it is manufactured by immunizing a rabbit with purified ceruloplasmin containing holoceruloplasmin as an antigen. On the other hand, the ceruloplasmin-specific monoclonal antibody is manufactured by immunizing a mouse with purified ceruloplasmin containing holoceruloplasmin as an antigen in order to obtain spleen cells that produce antibodies. The spleen cells are fused with myeloma cells Sp2/0-Ag14 according to a conventional fusion method, and the fused cells are cultured in a HAT-selecting media. Then, hybridoma cells that produce antibodies are selected by applying the enzyme-linked immunosorbent assay, and monoclonal antibody-producing hybridoma cells are obtained by applying a limiting dilution method.

The culture supernatant containing the monoclonal antibody secreted from the hybridoma cells is reacted with ceruloplasmin, wherein, in one embodiment, it neutralizes oxidase activity of holoceruloplasmin. In this way, hybridoma cell clones producing a holoceruloplasmin-specific antibody are selected. In other embodiments, the monoclonal antibody does not neutralize oxidase activity of holoceruloplasmin.

In addition, the monoclonal antibody and the polyclonal antibody, which are used as a secondary antibody, were conjugated with horseradish peroxidase to prepare antibodies necessary for the enzyme-linked immunosorbent assay, and with europium to prepare antibodies necessary for the dissociation-enhanced time-resolved fluoroimmunoassay.

The method for measuring holoceruloplasmin according to the enzyme-linked immonosorbent assay or the dissociation-enhanced time-resolved fluoroimmunoassay is comprised the steps of: manufacturing blood free of ceruloplasmin; manufacturing the standard blood spot and the control reference blood spot by adding purified ceruloplasmin containing the holoceruloplasmin to the blood at a predetermined concentration; and obtaining a standard curve based on the sandwich method using a standard blood spot and antibodies to measure holoceruloplasmin concentration in a specimen obtained from a Wilson's disease patient and a normal person, respectively.

A preferred embodiment of the present invention will now be described. It is also to be understood that the embodiment is provided for the purpose of illustration not limiting the scope of the present invention.

EXAMPLE 1

Manufacture of a Ceruloplasmin-Specific Polyclonal Antibody

In the example, purified human ceruloplasmin containing holoceruloplasmin was purchased from Sigma Co. in America. In order to produce an antigen specific polyclonal antibody, 400 μl of purified ceruloplasmin that had been dissolved in a phosphate-buffered saline at a concentration of 1 mg/ml was emulsified with the same amount of Freund's adjuvant purchased from BRL Co., and then the resultant was injected under the skin of a rabbit three times at 14-day intervals. Fourteen days after the last injection, 400 μl of purified ceruloplasmin that had been dissolved in a phosphate-buffered saline at the concentration of 1 mg/ml was injected to the rabbit through the ear vein, and seven days later, the blood of the rabbit was collected in accordance to a cardiac puncture method. The collected blood was left at room temperature for 30 minutes and 4° C. overnight to be completely condensed. Then, the condensed blood was centrifuged and serum was collected from the pure part of the solution. To this solution, ammonium sulfate was added, thereby making the final concentration of the solution be 40% for precipitating antibody. Later, the precipitate was dialyzed in 5 L of phosphate-buffered saline (pH 7.0) overnight and the antibody was purified by DEAE Affi-Gel Blue gel manufactured by Bio-Rad Co.

EXAMPLE 2

Manufacture of Ceruloplasmin-Specific Monoclonal Antibody

In order to manufacture the monoclonal antibody of the present invention, 100 μl of purified ceruloplasmin having the concentration of 1 mg/ml was emulsified with the same amount of Freund's adjuvant, and the resultant was injected to the abdomen of a BALB/c mouse at an age of 6 to 8 weeks for three times at 14-day intervals. After confirming that ceruloplasmin antibodies were produced after the last injection, the mouse was immunized by injecting 100 μg of ceruloplasmin dissolved in a phosphate-buffered saline in two weeks. Three days later, spleen cells extracted from the mouse were mixed with Sp2/0-Ag 14 myeloma cells at the ratio of 10:1. The mixture was left in polyethyleneglycol 1500 solution for 3 minutes to proceed cell fusion, and centrifuged at 1,200 rpm for 8 minutes to obtain cell precipitates. Then, the precipitates were floated on HAT/RPMI-1640 medium containing 10% fetal calf serum to make $3.5 \times 10^6$ cells per milliliter, and distributed to 96-well plates by 0.1 ml per well for culture in a 5% $CO_2$ culture fluid at 37° C. Three days later, the HAT/RPMI-1640 medium containing 10% fetal calf serum was added again to each well by 0.1 ml every four days, and approximately half of the medium was replaced with a fresh medium.

Following the HAT selection, the enzyme-linked immunosorbent assay was used to find out if the hybridoma cells successfully produced antibodies as intended. That is, 0.1 μg/ml of the ceruloplasmin used for immunization as aforementioned was diluted in 0.01 M carbonate-bicarbonate pH 9.6, and 50 μl of the diluted solution was put into each well, which was later coated overnight at 4° C. Then, it was washed by PBST (phosphate-buffered saline, 0.05% Tween 20) three times, and reacted with 1% albumin at room temperature for two hours for blocking. Particularly, 50 µl of the culture soup of the cells was put into each well for another two-hour reaction and washed by PBST. A secondary antibody, biotin conjugated anti-mouse immunoglobulin antibody, where biotin was attached, was 1:1000 diluted in 1% BSA-PBST to make the final concentration of 1 µg/ml, and 50 µl thereof was additionally put into each well for reaction at 37° C. for one hour. The PBST was again used for cleansing the mixture in each well three times. Next, 50 µl of streptavidin-horseradish peroxidase diluted in 1% BSA-PBST by 1000 times was put into each well for another reaction at 37° C. for 30 minutes and cleansed by PBST four times. As for a substrate for an enzyme reaction, 50 µl of tetra-methylbenzidine (TMB) solution was put into each well for a reaction at room temperature. Following the reaction, 2N-sulfuric acid was added to stop the reaction, and absorbance of the resultant was measured by ELISA reader at a wavelength of 450 nm. When it was observed that ceruloplasmin antibody was produced, the cells obtained from the wells that showed a positive reaction went through the subcloning three times by the limiting dilution method until each well has 0.3 cell, and was cultured to obtain hybridoma cells that produce an anti-ceruloplasmin monoclonal antibody.

EXAMPLE 3

Confirmation of Ceruloplasmin Oxidase Activity Neutralization by Antibody

The mixture of 10 µg of purified ceruloplasmin and the same volume of each of different hybridoma supernatants was reacted together at 37° C. for 30 minutes, and electrophoresed using nonparametric polyacrylamide gel at 4° C. After the electrophoresis, the sodium acetate (pH 5.7) containing 1 mg/ml of p-phenylenediamine dyed over the gel at 37° C. for two hours to confirm the oxidase activity of ceruloplasmin, and was decolorized using 50% ethanol (FIG. 1).

As shown in FIG. 1, the purified ceruloplasmin oxidized p-phenylenediamin by self-oxidase activity and formed a purple band. On the other hand, in the mixed solution of ceruloplasmin with a ceruloplasmin-specific antibody did not form the purple band since the antibody neutralized the oxidase activity of ceruloplasmin. Therefore, the monoclonal antibody manufactured in Example 2 specifically binds to ceruloplasmin having an oxidase activity.

EXAMPLE 4

Purification of Ceruloplasmin-Specific Monoclonal Antibody

Hybridoma cells producing the ceruloplasmin-specific monoclonal antibody selected from Example 3 were cultured in T75 flask containing RPMI medium containing 10% fetal bovine serum and cultured in 5% $CO_2$ incubator at 37° C. for 7 days. Later, the cells were centrifuged to obtain supernatant, and ammonium sulfate was added to the culture fluid, thereby making the final concentration of the solution be 50% for precipitating antibody. Then, the solution was dialyzed in 5 L of phosphate-buffered saline (pH 7.0) overnight and the antibody was purified by DEAE Affi-Gel Blue gel.

EXAMPLE 5

Manufacture of Anti-Ceruloplasmin Antibody Conjugated with Horseradish Peroxidase Five (5) mg of the purified antibody obtained from Examples 1 or 4 and 5 mg of horseradish peroxidase were dialyzed in 0.1M phosphate buffer (pH 6.8) overnight. Additionally added was glutaraldehyde solution that had been diluted by 0.1M phosphate-buffered saline until the final concentration becomes 0.1%. While slowly stirring the mixture for three hours at room temperature, 2M glycin was added to make the final concentration of 0.1M and left aside for two hours. The mixture was again dialyzed in phosphate-buffered saline for overnight and glycerol was finally added at the same volume with the mixture obtained from 30-minute centrifugation at 10,000 g, and the resultant was stored at −20° C.

EXAMPLE 6

Manufacture of Anti-Ceruloplasmin Antibody Conjugated with Europium

One (1) mg of the pure antibody obtained from Examples 1 or 4 was dialyzed in 0.1M sodium carbonate buffer (pH 9.3) overnight, and condensed until the final concentration of 4 mg/ml. 250 µl of the antibody was slowly added to 0.2 mg of chelated europium $N^1$-(p-isothiocyanate benzyl)-diethylentriamine-$N^1,N^2,N^3,N^3$-tetra acetate (DTTA), and the reaction was continued at 4° C. overnight. Then, the resultant was gel filtered using Superdex 200 column (distributed by Amersham Co.) and TSA buffer (50 mmol/L Tris-HCl (pH 7.8), 0.9% of NaCl, 0.0% of Sodium azide). Later, albumin was added to make the final concentration of 0.1% and the final resultant was stored at −20° C.

EXAMPLE 7

Manufacture of Ceruloplasmin-Free Blood

A blood sample was centrifuged at 3,000 rpm for 10 minutes and plasma in the upper layer was removed. After adding phosphate-buffered saline, the centrifugation was repeated using the same method. The blood without plasma was then washed by phosphate-buffered saline for nine times using the same centrifugation method. The supernatant was discarded and ceruloplasmin-free red blood cells (RBCs) were obtained.

EXAMPLE 8

Manufacture of Standard Blood Spot

Ceruloplasmin was added at known concentrations to the ceruloplasmin-free blood obtained from Example 7, to decide a range of standard concentration. Here, the concentrations of standard ceruloplasmin were 0 mg/dl, 1 mg/dl, 5 mg/dl, 20 mg/dl and 50 mg/dl for enzyme-linked immunosorbent assay and 0 mg/dl, 1 mg/dl, 5 mg/dl, 10 mg/dl, 20 mg/dl and 30 mg/dl for dissociation-enhanced time-resolved fluoroimmunoassay. In order to manufacture standard blood spot, the blood of Example 7 and ceruloplasmin solutions with known concentrations were mixed together at the ratio of 1:1, and the original hematocrit was adjusted finally. Therefore, when each standard concentration solution is manufactured, ceruloplasmin was doubly condensed and mixed with the blood plasma obtained from Example 7. Later, the mixture was spotted on filter paper, which was dried at room temperature for overnight.

EXAMPLE 9

Manufacture of Control Reference Blood Spot

The same procedure of Example 8 was repeated except that the control ceruloplasmin concentrations are 3 mg/dl (1.40–4.80), 7 mg/dl (5.0–9.0) and 15 mg/dl (10.5–19.5). Similar to the method for manufacturing the standard blood spot, the blood and ceruloplasmin with the known concentration were mixed at the ratio of 1:1. Later, the mixture was spotted on filter paper and it was dried at room temperature for overnight.

EXAMPLE 10

Measurement of Ceruloplasmin from Blood Spot According to Enzyme-Linked Immunosorbent Assay (Sandwich Method of Monoclonal Antibody-Monoclonal Antibody)

In order to measure the amount of ceruloplasmin in a blood spot, a holoceruloplasmin-specific monoclonal antibody obtained from Examples 2 and 4 was diluted by 0.05M carbonate-bicarbonate buffer to 2 µg/ml of concentration. 100 µl of diluted antibody was put into each well and coated over at 4° C. overnight. Then, it was washed by phosphate-buffered saline containing 0.05% Tween 20 four times and reacted with phosphate-buffered saline containing 3% albumin at room temperature for 5–8 hours. After another cleansing according to the above, 1.5 mm diameter of punched blood spot was put into each well. Here, 100 µl of an eluent, phosphate-buffered saline containing 1% albumin was added to each well enough to immerse the blood spots and reacted together at 4° C. overnight. After removing the blood spots, the well was washed by phosphate-buffered saline containing 0.05% Tween 20 four times. Then, the bounded ceruloplasmin was reacted with 100 µl of the secondary monoclonal antibody conjugated with horseradish peroxidase of Example 5, prepared by diluting at the ratio of 1:500 with the secondary monoclonal antibody and phosphate-buffered saline containing 1% albumin and 0.05% Tween 20 for 90 minutes, at room temperature. Again, the antibody was cleansed by phosphate buffer saline containing 0.05% Tween 20 six times. As for a substrate for an enzyme reaction, 100 µl of TMB solution was added to each well for the reaction at room temperature for 15 minutes, and later, the reaction was stopped by adding 100 µl of 1N-hydrochloric acid. The measurement of absorbance was accomplished at a wavelength of 450 nm using ELISA reader.

EXAMPLE 11

Measurement of Ceruloplasmin from Blood Spot According to Dissociation-Enhanced Time-Resolved Fluoroimmunoassay (Sandwich Method of Monoclonal Antibody-Monoclonal Antibody)

In order to measure the amount of ceruloplasmin in a blood spot, anti holoceruloplasmin-specific monoclonal antibody obtained from Examples 2 and 4 was diluted by 0.05M carbonated bicarbonate buffer at 2 µg/ml. 100 µl of diluted antibody was put into each well and coated over at 4° C. overnight. Then, it was washed by 50 mmol/L of Tris-HCl (pH 7.8) buffer containing 0.1% Tween 20 and 0.9% of NaCl four times and reacted with Tris-HCl (pH 7.8) buffer containing 3% albumin at room temperature for 5–8 hours. After another washing according to the above, 1.5 mm diameter of punched blood spot was put into each well. Here, 100 µl of an eluent, DELFIA assay buffer (distributed by Wallac Co.) was added to each well enough to immerse the blood spots and reacted together at 4° C. overnight. After removing the blood spots, the wells were washed by Tris-HCl (pH 7.8) buffer containing 0.1% Tween 20 and 0.9% NaCl. Then, the bounded ceruloplasmin in the cell was reacted with the secondary monoclonal antibody conjugated with europium of Example 6 diluted by DELFIA assay buffer to make the concentration of 250 ng/ml for 90 minutes at room temperature. Again, the wells were washed by Tris-HCl (pH 7.8) containing 0.1% Tween 20 and 0.9% NaCl four times. Finally, 200 µl of DELFIA enhancement solution (distributed by Wallac Co.) was added to each well and two minutes later, copy number of europium was measured using a time-resolved fluorometry.

EXAMPLE 12

Measurement of Ceruloplasmin from Blood Spot According to Enzyme-Linked Immunosorbent Assay (Sandwich Method of Monoclonal Antibody-Polyclonal Antibody)

The same procedure of Example 10 was employed in order to measure the amount of ceruloplasmin in the blood spot except that the polyclonal antibody conjugated with horseradish peroxidase obtained from Examples 1 and 5 was used for the secondary antibody.

EXAMPLE 13

Measurement of Ceruloplasmin from Blood Spot According to Dissociation-Enhanced Time-Resolved Fluoroimmunoassay (Sandwich Method of Monoclonal Antibody-Polyclonal Antibody)

The same procedure of Example 11 was employed in order to measure the amount of ceruloplasmin in the blood spot except that the polyclonal antibody conjugated with europium obtained from Examples 1 and 6 was used for the secondary antibody.

EXAMPLE 14

Measurement of Ceruloplasmin from Blood Spot According to Enzyme-Linked Immunosorbent Assay (Sandwich Method of Polyclonal Antibody-Polyclonal Antibody)

The same procedure of Example 10 was employed in order to measure the amount of ceruloplasmin in the blood spot except that the polyclonal antibody obtained from Example 1 was used for the coating antibody and polyclonal antibody conjugated with horseradish peroxidase obtained from Examples 1 and 5 was used for the secondary antibody, respectively.

EXAMPLE 15

Measurement of Ceruloplasmin from Blood Spot According to Dissociation-Enhanced Time-Resolved Fluoroimmunoassay (Sandwich Method of Polyclonal Antibody-Polyclonal Antibody)

The same procedure of Example 11 was employed in order to measure the amount of ceruloplasmin in the blood spot except that the polyclonal antibody obtained from Example 1 was used for the coating antibody and polyclonal antibody conjugated with europium obtained from Examples 1 and 6 was used for the secondary antibody, respectively.

EXAMPLE 16

Figure 2:
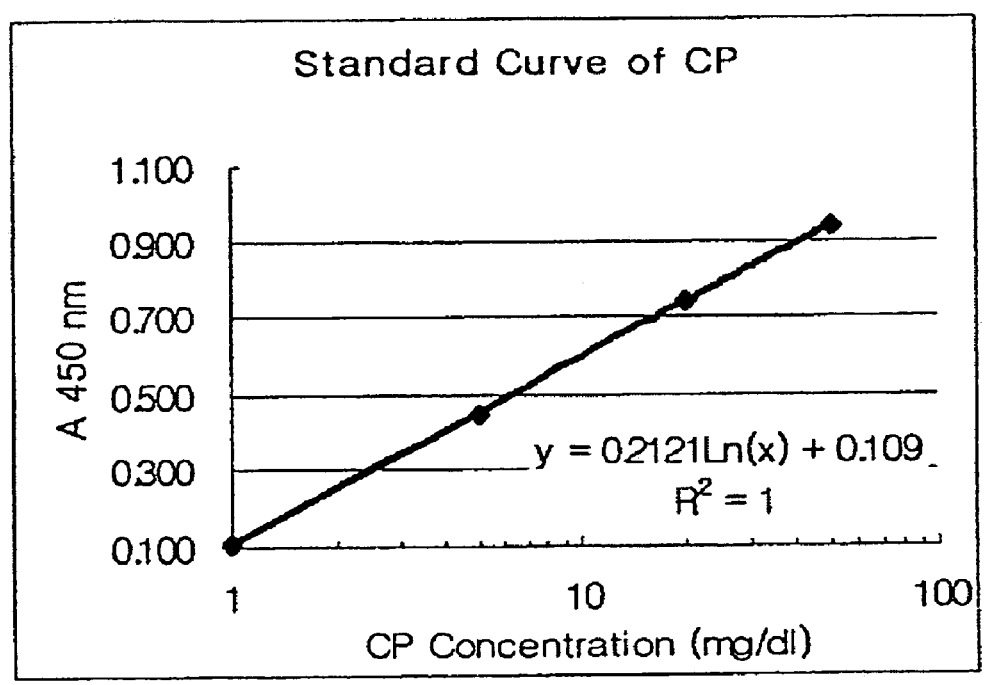
FIG. 2 is an absorbance standard curve of holoceruloplasmin concentrations.

Quantitative Analysis of Ceruloplasmin on Normal Controls and Wilson's Disease Patients According to Enzyme-Linked Immunosorbent Assay Blood was collected from 5 normal controls and 12 of Wilson's disease patients in order to make blood spots. After drying the blood spots overnight, the ceruloplasmin concentration was measured based on the standard concentration curve according to the method explained in Example 10 (FIG. 2).

EXAMPLE 17

Figure 3:
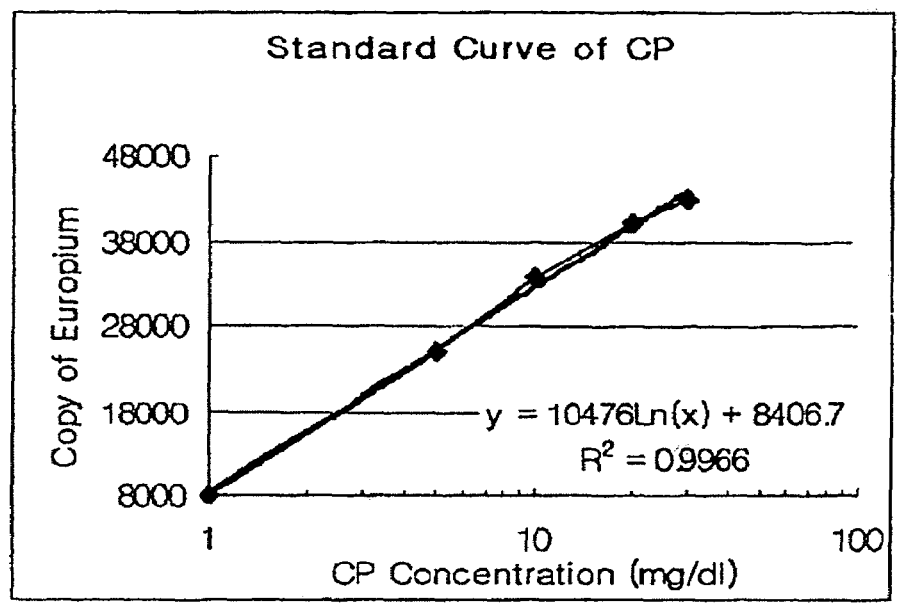
FIG. 3 is a fluorescence standard curve of holoceruloplasmin concentrations.

Quantitative Analysis of Ceruloplasmin on Normal Controls and Wilson's Disease Patients According to Dissociation-Enhanced Time-Resolved Fluoroimmunoassay Blood was collected from 5 normal controls and 12 of Wilson's disease patients in order to make blood spots. After drying the blood spots overnight, the ceruloplasmin concentration was measured based on the standard concentration curve according to the method explained in Example 11 (FIG. 3).

Figure 4:
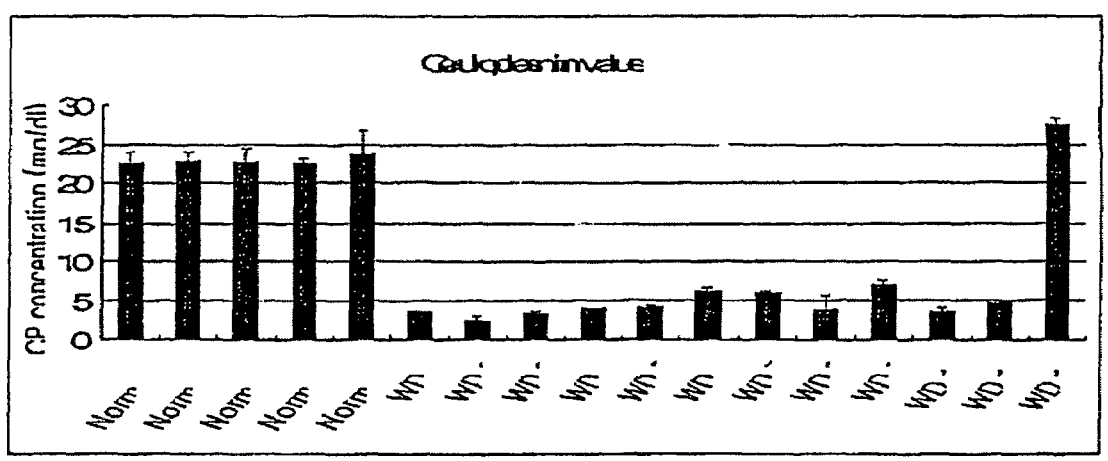
FIG. 4 shows the holoceruloplasmin levels of normal controls (Norm) and of Wilson's disease patients (WD), which were determined using dissociation-enhanced time-resolved fluoroimmunoassay.

As shown in FIG. 4, the ceruloplasmin concentration of the Wilson's disease patients (WD) was noticeably lower than that of the normal controls (Norm), which proves that the diagnosis reagent of the present invention is very effective to diagnose Wilson's disease at an early stage of clinical course. However, as in the case of the Wilson's disease patient (WD 12) illustrated in FIG. 4, 5% of patients in Wilson's disease would exhibit the normal ceruloplasmin concentration. In such cases, early diagnosis could be difficult with this method.

EXAMPLE 18

Manufacture of Ceruloplasmin-Specific Monoclonal Antibody which does not Neutralize Oxidase Activity of Holoceruloplasmin In order to manufacture the monoclonal antibody which does not neutralize oxidase activity of holoceruloplasmin, 100 µl of purified ceruloplasmin having the concentration of 1 mg/ml was emulsified with the same amount of Freund's adjuvant, and the resultant was injected to the abdomen of a BALB/c mouse at an age of 6 to 8 weeks for three times at 14-day intervals. After confirming that ceruloplasmin antibodies were produced after the last injection, the mouse was immunized by injecting 100 µg of ceruloplasmin dissolved in a phosphate-buffered saline in two weeks. Three days later, spleen cells extracted from the mouse were mixed with Sp2/0-Ag 14 myeloma cells at the ratio of 10:1. The mixture was left in polyethyleneglycol 1500 solution for 3 minutes to proceed cell fusion, and centrifuged at 1,200 rpm for 8 minutes to obtain cell precipitates. Then, the precipitates were floated on HAT/RPMI-1640 medium containing 10% fetal calf serum to make $3.5 \times 10^6$ cells per milliliter, and distributed to 96-well plates by 0.1 ml per well for culture in a 5% $CO_2$ culture fluid at 37° C. Three days later, the HAT/RPMI-1640 medium containing 10% fetal calf serum was added again to each well by 0.1 ml every four days, and approximately half of the medium was replaced with a fresh medium.

Following the HAT selection, the enzyme-linked immunosorbent assay was used to find out if the hybridoma cells successfully produced antibodies as intended. That is, 0.1 µg/ml of the ceruloplasmin used for immunization as aforementioned was diluted in 0.01M carbonate-bicarbonate pH 9.6, and 50 µl of the diluted solution was put into each well, which was later coated overnight at 4° C. Then, it was washed by PBST (phosphate-buffered saline, 0.05% Tween 20) three times, and reacted with 1% albumin at room temperature for two hours for blocking. Particularly, 50 µl of the culture soup of the cells was put into each well for another two-hour reaction and washed by PBST. A secondary antibody, biotin conjugated anti-mouse immunoglobulin antibody, where biotin was attached, was 1:1000 diluted in 1% BSA-PBST to make the final concentration of 1 µg/ml, and 50 µl thereof was additionally put into each well for reaction at 37° C. for one hour. The PBST was again used for cleansing the mixture in each well three times. Next, 50 µl of streptavidin-horseradish peroxidase diluted in 1% BSA-PBST by 1000 times was put into each well for another reaction at 37° C. for 30 minutes and cleansed by PBST four times. As for a substrate for an enzyme reaction, 50 µl of tetra-methylbenzidine (TMB) solution was put into each well for a reaction at room temperature. Following the reaction, 2N-sulfuric acid was added to stop the reaction, and absorbance of the resultant was measured by ELISA reader at a wavelength of 450 nm. When it was observed that ceruloplasmin antibody was produced, the cells obtained from the wells that showed a positive reaction went through the subcloning three times by the limiting dilution method until each well has 0.3 cell, and was cultured to obtain hybridoma cells that produce an anti-ceruloplasmin monoclonal antibody.

Figure 5:
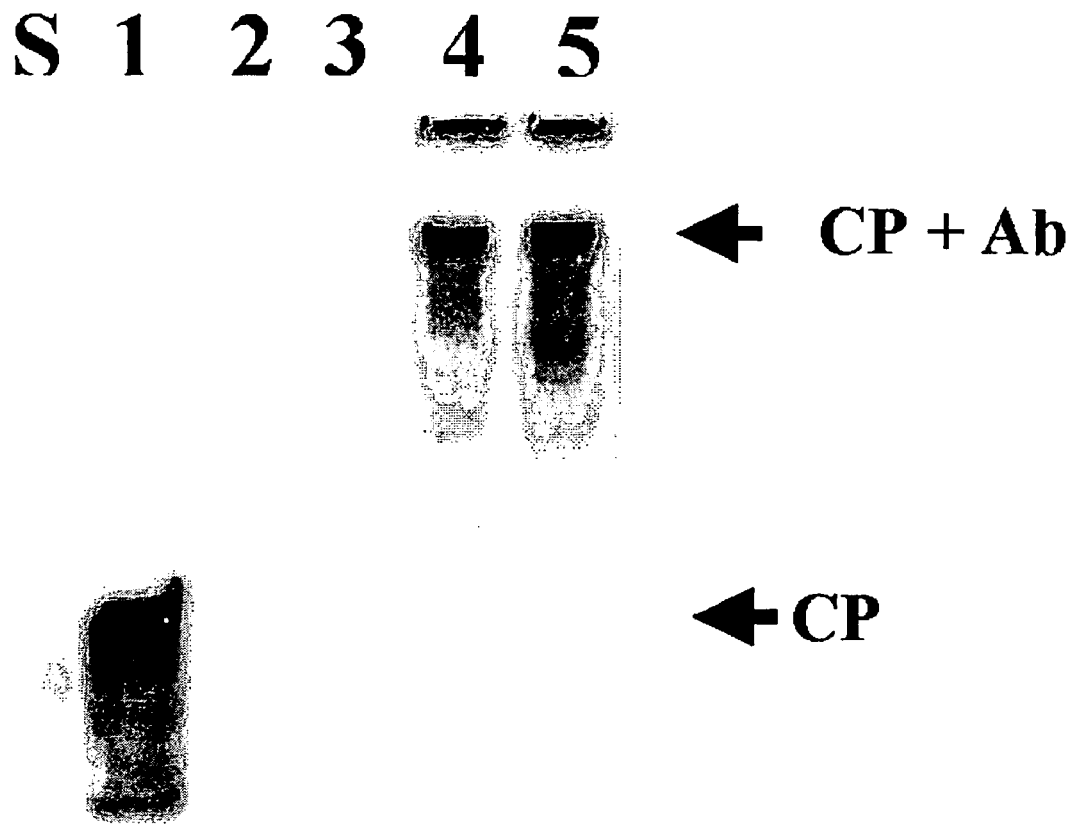
FIG. 5 shows that a ceruloplasmin mixed with monoclonal antibody 2-1.1 (lane 4) or 1-2.1 (lane 5) does not lose its oxidase activity.

The mixture of 10 µg of purified ceruloplasmin and the same volume of each of different hybridoma supernatants was reacted together at 37° C. for 30 minutes, and electrophoresed using nonparametric polyacrylamide gel at 4° C. After the electrophoresis, the sodium acetate (pH 5.7) containing 1 mg/ml of p-phenylenediamine dyed over the gel at 37° C. for two hours to confirm the oxidase activity of ceruloplasmin, and was decolorized using 50% ethanol (FIG. 5). In FIG. 5, lanes 4 and 5, containing the complexes of ceruloplasmin-monoclonal antibodies, show purple bands, indicating the monoclonal antibodies do not neutralize oxidase activity of the ceruloplasmin indicating that these antibodies do not bind to the epitope responsible for oxidase activity of ceruloplasmin.

Two antibodies which are specific to ceruloplasmin, but do not neutralize oxidase activity of holoceruloplasmin were designated as "2-1.1" and "1-2.1." These monoclonal antibodies did not show any significant differences in measuring the ceruloplasmin from a blood spot.

It was reported that the use of an antibody recognizing an oxidase epitope renders a more sensitive assay. The mean value for ceruloplasmin in the blood spot was 12.4±3.95 mg/dl when an antibody recognizing an oxidase epitope was employed. However, the mean value was much higher with 30.5±9.5 mg/dl when the antibody which does not recognize oxidase activity of ceruloplasmin was used. Given the fact that normal reference range for serum ceruloplasmin value is between 20–45 mg/dl and some of patients with Wilson disease could have moderately reduced ceruloplasmin, not markedly reduced as in most cases, the low normal range could obviously hamper the detection of Wilson disease resulting in high false negative rate.

Hybridoma cell lines (WD-2.1.1 and WD-1.2) producing these monoclonal antibodies were deposited under the terms of the Budapest Treaty with the Korean Collection for Type Cultures (KCTC) located at 52, Oun-dong, Yusong-Ku, Daejon, Korea on Nov. 9, 2004 under the accession numbers of KCTC 10718BP and KCTC 10719BP, respectively.

The deposits made in connection with the filing of the patent application(s) for the present invention were made for a term of at least thirty (30) years and at least five (5) years after the most recent request for the furnishing of a sample of the deposit was received by the depository. Access to the deposit is available during pendency of the patent application making reference to the deposit. Subject to 37 C.F.R. § 1.808 (b), all restrictions imposed b the depositor on the availability to the public of the deposited material will be irrevocably removed upon the granting of the patent.

EXAMPLE 19

Purification of Holoceruloplasmin-Specific Monoclonal Antibody

Hybridoma cells producing the holoceruloplasmin-specific monoclonal antibody selected from Example 18 were cultured in T75 flask containing RPMI medium containing 10% fetal bovine serum and cultured in 5% $CO_2$ incubator at 37° C. for 7 days. Later, the cells were centrifuged to obtain supernatant, and ammonium sulfate was added to the culture fluid, thereby making the final concentration of the solution be 50% for precipitating antibody. Then, the solution was dialyzed in 5L of phosphate-buffered saline (pH 7.0) overnight and the antibody was purified by DEAE Affi-Gel Blue gel.

EXAMPLE 20

Manufacture of Anti-Ceruloplasmin Antibody Conjugated with Horseradish Peroxidase Five (5) mg of the purified antibody obtained from Example 19 and 5 mg of horseradish peroxidase were dialyzed in 0.1M phosphate-buffer (pH 6.8) overnight. Additionally added was glutaraldehyde solution that had been diluted by 0.1M phosphate-buffered saline until the final concentration becomes 0.1%. While slowly stirring the mixture for three hours at room temperature, 2M glycin was added to make the final concentration of 0.1M and left aside for two hours. The mixture was again dialyzed in phosphate-buffered saline for overnight and glycerol was finally added at the same volume with the mixture; obtained from 30-minute centrifugation at 10,000 g, and the resultant was stored at −20° C.

EXAMPLE 21

Manufacture of Anti-Ceruloplasmin Antibody Conjugated with Europium

One (1) mg of the pure antibody obtained from Example 19 was dialyzed in 0.1M sodium carbonate buffer (pH 9.3) overnight, and condensed until the final concentration of 4 mg/ml. 250 µl of the antibody was slowly added to 0.2 mg of chelated europium $N^1$-(p-isothiocyanate benzyl)-diethylentriamine-$N^1,N^2,N^3,N^3$-tetra acetate (DTTA), and the reaction was continued at 4° C. overnight. Then, the resultant was gel filtered using Superdex 200 column (distributed by Amersham Co.) and TSA buffer (50 mmol/L Tris-HCl (pH 7.8), 0.9% of NaCl, 0.0% of Sodium azide). Later, albumin was added to make the final concentration of 0.1% and the final resultant was stored at −20° C.

EXAMPLE 22

Measurement of Ceruloplasmin from Blood Spot According to Enzyme-Linked Immunosorbent Assay (Sandwich Method of Monoclonal Antibody-Monoclonal Antibody)

In order to measure the amount of ceruloplasmin in a blood spot, a holoceruloplasmin-specific monoclonal antibody 2-1.1 was diluted by 0.05M carbonate-bicarbonate buffer to 2 µg/ml of concentration. 100 µl of diluted antibody was put into each well and coated over at 4° C. overnight. Then, it was washed by phosphate-buffered saline containing 0.05% Tween 20 four times and reacted with phosphate-buffered saline containing 3% albumin at room temperature for 5–8 hours. After another cleansing according to the above, 1.5 mm diameter of punched blood spot was put into each well. Here, 100 µl of an eluent, phosphate-buffered saline containing 1% albumin was added to each well enough to immerse the blood spots and reacted together at 4° C. overnight. After removing the blood spots, the well was washed by phosphate-buffered saline containing 0.05% Tween 20 four times. Then, the bounded ceruloplasmin was reacted with 100 µl of the secondary monoclonal antibody 1-2.1, which was conjugated with a peroxidase, prepared by diluting at the ratio of 1:500 with the secondary monoclonal antibody and phosphate-buffered saline containing 1% albumin and 0.05% Tween 20 for 90 minutes, at room temperature. Again, the antibody was cleansed by phosphate buffer saline containing 0.05% Tween 20 six times. As for a substrate for an enzyme reaction, 100 µl of TMB solution was added to each well for the reaction at room temperature for 15 minutes, and later, the reaction was stopped by adding 100 µl of 1N-hydrochloric acid. The measurement of absorbance was accomplished at a wavelength of 450 nm using an ELISA reader.

EXAMPLE 23

Measurement of Ceruloplasmin from Blood Spot According to Dissociation-Enhanced Time-Resolved Fluoroimmunoassay (Sandwich Method of Monoclonal Antibody-Monoclonal Antibody)

In order to measure the amount of ceruloplasmin in a blood spot, anti holoceruloplasmin-specific monoclonal antibody 2-1.1 was diluted by 0.05M carbonated bicarbonate buffer at 2 μg/ml. 100 μl of diluted antibody was put into each well and coated over at 4° C. overnight. Then, it was washed by 50 mmol/L of Tris-HCl (pH 7.8) buffer containing 0.1% Tween 20 and 0.9% of NaCl four times and reacted with Tris-HCl (pH 7.8) buffer containing 3% albumin at room temperature for 5–8 hours. After another washing according to the above, 1.5 mm diameter of punched blood spot was put into each well. Here, 100 μl of an eluent, DELFIA assay buffer (distributed by Wallac Co.) was added to each well enough to immerse the blood spots and reacted together at 4° C. overnight. After removing the blood spots, the wells were washed by Tris-HCl (pH 7.8) buffer containing 0.1% Tween 20 and 0.9% NaCl. Then, the bounded ceruloplasmin in the cell was reacted with the secondary monoclonal antibody 1-2.1, which was conjugated with europium, diluted by DELFIA assay buffer to make the concentration of 250 ng/ml for 90 minutes at room temperature. Again, the wells were washed by Tris-HCl (pH 7.8) containing 0.1% Tween 20 and 0.9% NaCl four times. Finally, 200 μl of DELFIA enhancement solution (distributed by Wallac Co.) was added to each well and two minutes later, copy number of europium was measured using a time-resolved fluorometry.

EXAMPLE 24

Measurement of Ceruloplasmin from Blood Spot According to Enzyme-Linked Immunosorbent Assay (Sandwich Method of Monoclonal Antibody-Polyclonal Antibody)

The same procedure of Example 10 is employed in order to measure the amount of ceruloplasmin in the blood spot except that the polyclonal antibody conjugated with horseradish peroxidase obtained from Example 5 is used for the secondary antibody.

EXAMPLE 25

Measurement of Ceruloplasmin from Blood Spot According to Dissociation-Enhanced Time-Resolved Fluoroimmunoassay (Sandwich Method of Monoclonal Antibody-Polyclonal Antibody)

The same procedure of Example 11 is employed in order to measure the amount of ceruloplasmin in the blood spot except that the polyclonal antibody conjugated with europium obtained from Example 6 is used for the secondary antibody.

EXAMPLE 26

Quantitative Analysis of Ceruloplasmin on Normal Controls and Wilson's Disease Patients According to Enzyme-Linked Immunosorbent Assay Blood is collected from 5 normal controls and 12 of Wilson's disease patients in order to make blood spots. After drying the blood spots overnight, the ceruloplasmin concentration is measured based on the standard concentration curve according to the method explained in Example 22.

EXAMPLE 27

Quantitative Analysis of Ceruloplasmin on Normal Controls and Wilson's Disease Patients According to Dissociation-Enhanced Time-Resolved Fluoroimmunoassay Blood is collected from 5 normal controls and 12 of Wilson's disease patients in order to make blood spots. After drying the blood spots overnight, the ceruloplasmin concentration is measured based on the standard concentration curve according to the method explained in Example 23. The patient with Wilson disease shows significant lower concentration of ceruloplasmin compared to that of normal controls.

In conclusion, the present invention provides the method of quantitative analysis for ceruloplasmin in the blood spot collected on filter papers from young infants or children using the enzyme-linked immunosorbent assay or the dissociation-enhanced time-resolved fluoroimmunoassay, and could be used as screening kit for an early diagnosis of Wilson's disease. According to the present invention, only a few drops of blood punctured by lancet are enough to diagnose the disease, making more efficient as a mass screening measured than conventional assay such as radial immunodiffusion assay and immunoturbidimetric assay.

The Wilson's disease diagnosis reagent and the Wilson's disease diagnosis kit of the present invention make it possible to measure ceruloplasmin concentration in the blood spot based on the standard concentration curve obtained through the enzyme-linked immunosorbent assay or the dissociation-enhanced time-resolved fluoroimmunoassay using the holo-ceruloplasmin-specific polyclonal antibody, a holoceruloplasmin-specific monoclonal antibody, a standard blood spot and a control reference blood spot. Accordingly, since the method of the present invention is very convenient to collect, carry and store the specimen required for the mass screening, it is more possible to analyze the large number of samples at once and it is now possible that the mass screening of Wilson's disease can be applied with one invented method.

While the invention has been shown and described with reference to certain preferred embodiments thereof, it will be understood by those skilled in the art that various changes in form and details may be made therein without departing from the spirit and scope of the invention as defined by the appended claims.

What is claimed is:

1. A Wilson's disease screening kit reagent, comprising a ceruloplasmin-specific primary monoclonal antibody; a ceruloplasmin-specific secondary monoclonal antibody which recognizes an epitope other than an epitope recognized by the primary monoclonal antibody, wherein the primary and secondary monoclonal antibodies do not neutralize oxidase activity of ceruloplasmin and are an antibody having all of the identifying properties and characteristics of the monoclonal antibody which is secreted from the hybridoma WD-2.1.1 (KCTC 10718BP) or hybridoma WD-1.2 (KCTC 10719BP).

2. A Wilson's disease screening kit for measuring a ceruloplasmin level in a dried blood spot sample, comprising a ceruloplasmin-specific primary monoclonal antibody; and a ceruloplasmin-specific secondary monoclonal antibody which recognizes an epitope other than an epitope that recognized by the primary monoclonal antibody and is conjugated with an enzyme or a lanthanide, wherein said primary and secondary monoclonal antibodies do not neutralize oxidase activity of ceruloplasmin and at least one of said primary and secondary monoclonal antibodies are an antibody having all of the identifying properties and characteristics of the monoclonal antibody which is secreted from the hybridoma WD-2.1.1 (KCTC 10718BP) or hybridoma WD-1.2 (KCTC 10719BP), said blood spot is brought into contact with the primary monoclonal antibody and the secondary monoclonal antibody, and the ceruloplasmin level is determined by comparing the strength of the enzyme of the secondary antibody bound to ceruloplasmin with a standard absorbance curve of ceruloplasmin concentrations.

3. The Wilson's disease screening kit of claim 1, wherein said blood spot is a punched filter paper, which is prepared by spotting a blood sample of a subject on the filter paper, followed by drying.

* * * * *